(12) United States Patent
Jung et al.

(10) Patent No.: US 7,223,355 B2
(45) Date of Patent: May 29, 2007

(54) FUNCTIONAL ADDITIVE HAVING UV-ABSORBING SUBSTITUENT AND INK COMPOSITION CONTAINING THE SAME

(75) Inventors: Yeon-kyoung Jung, Seoul (KR); Soung-min Ryu, Gyeonggi-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 171 days.

(21) Appl. No.: 10/704,561

(22) Filed: Nov. 12, 2003

(65) Prior Publication Data

US 2004/0103820 A1    Jun. 3, 2004

(30) Foreign Application Priority Data

Nov. 14, 2002    (KR) .................... 10-2002-0070656

(51) Int. Cl.
*C08K 5/05*    (2006.01)
*C08K 5/06*    (2006.01)
*C09K 3/00*    (2006.01)

(52) U.S. Cl. ...................... 252/393; 252/385; 524/376

(58) Field of Classification Search ................ 252/393, 252/385; 524/376
See application file for complete search history.

(56) References Cited

U.S. PATENT DOCUMENTS 6,346,595 B1    2/2002    O'Lenick, Jr.

FOREIGN PATENT DOCUMENTS

| JP | 60-260532 | 12/1985 |
| WO | 01/87822 | 11/2001 |

OTHER PUBLICATIONS

Korean Office Action for corresponding Korean Patent Application 10-2002-0070656, issued May 17, 2005.

*Primary Examiner*—Kriellion Sanders
(74) *Attorney, Agent, or Firm*—Staas & Halsey LLP

(57) ABSTRACT

A 2-methoxyphenol derivative and an ink composition containing the 2-methoxyphenol derivative, an aqueous medium, and a colorant enhance light resistance by absorbing ultraviolet (UV) light, provide wettability and stabilize a colorant. The ink composition prepared using the 2-methoxyphenol derivative also has improved light resistance, wettability and stabilizes a colorant and does not require an additional light-resistant agent.

5 Claims, No Drawings

FUNCTIONAL ADDITIVE HAVING UV-ABSORBING SUBSTITUENT AND INK COMPOSITION CONTAINING THE SAME

CROSS-REFERENCE TO RELATED APPLICATIONS

This application claims the priority of Korean Patent Application No. 2002-70656, filed on Nov. 14, 2002, in the Korean Intellectual Property Office, the disclosure of which is incorporated herein in its entirety by reference.

BACKGROUND OF THE INVENTION

1. Field of the Invention

The present invention relates to a light-resistant additive and an ink composition containing the same, and more particularly, to a light-resistant additive further having wettability and the ability to stabilize a colorant and an ink composition containing the light-resistant additive.

2. Description of the Related Art

In general, colored ink-jet ink compositions are composed of a colorant, such as a dye or a pigment, a stabilizer and a dispersant, which are used to improve the stability and dispersibiility of the colorant, an organic solvent, and a wetting agent.

Images printed using such an ink composition are exposed to visible light and ultraviolet (UV) light in the air. When these images are exposed to UV light for an extended period of time, since UV light has a higher energy level than visible light, various blemishes develop. For example, the whiteness of printing media deteriorates and changes to yellow. In addition, color images printed using an ink composition having poor light resistance are liable to bleach or discolor. To solve these problems, there is a need to add to ink compositions a light-resistant additive that blocks or absorbs UV light.

The use of a large molecular weight silicon compound as such a light-resistant additive is disclosed in U.S. Pat. No. 6,346,595. However, this silicon compound is not miscible with other components of an ink composition and, due to the large molecular weight, greatly affects the physical properties, for example, the viscosity, of the composition even when the amount of the silicon compound is slightly changed. Accordingly, it is difficult to adjust the amount of the additive used. In addition, although the polymer includes hydrophilic groups in its molecular structure, the hydrophilic fraction with respect to the total amount of the composition is too small to dissolve the compound sufficiently in water, and more time is required to dissolve the additive. Furthermore, the UV absorbing additive reacts with a colorant or other additives in the composition when stored for a long time, leads to phase separation, and deteriorates long-term storage stability.

SUMMARY OF THE INVENTION

The present invention provides a 2-methoxyphenol derivative that enhances light resistance, provides wettability and stabilizes a colorant.

The present invention also provides an ink composition containing the 2-methoxyphenol derivative, which provides effective light resistance and effective wettability and stabilizes a colorant when an additional light-resistant additive is used.

In one aspect, the present invention provides a 2-methoxyphenol derivative having formula (1) below, which has an ultraviolet (UV) light absorbing effect.

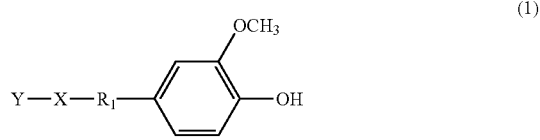

(1)

wherein $R_1$ is selected from among a substituted or unsubstituted $C_1$–$C_{20}$ alkylene group, a substituted or unsubstituted $C_1$–$C_{20}$ alkenylene group, a substituted or unsubstituted $C_1$–$C_{20}$ alkynylene group, a substituted or unsubstituted $C_6$–$C_{30}$ arylene group, a substituted or unsubstituted $C_6$–$C_{30}$ arylalkylene group, a substituted or unsubstituted $C_1$–$C_{30}$ heteroalkylene group, a substitute or unsubstituted $C_6$–$C_{30}$ heteroarylene group, and a substituted or unsubstituted $C_6$–$C_{30}$ heteroarylalkylene group;

X is selected from among —O—, —NR—, —N=N—, —S—, —P—, —C(=O)—NR—, —NR—C(=O)—, —S(=O)(=O)O—, —C(=O)O—, —O—C(=O)—, —P(=O)O—, —C(=O)—O—C(=O)—, —C(=O)—S—C(=O)—, —C(=)—NR—C(=O)—, —C(=NH)—O—C(=NH)—, —C(=S)—O—C(=S)—, —C(=NH)—NR—C(=NH)—, —C(=S)—NR—C(=S)—, —C(=NH)—S—C(=NH)—, and —C(=S)—S—C(=S)—;

R is a hydrogen atom or a $C_1$–$C_5$ alkyl group; and

Y is selected from among a substituted or unsubstituted $C_1$–$C_{20}$ alcohol, a substituted or unsubstituted $C_1$–$C_{20}$ diol, a substituted or unsubstituted $C_1$–$C_{20}$ triol, a substituted or unsubstituted $C_1$–$C_{20}$ polyhydric alcohol, a substituted or unsubstituted $C_2$–$C_{20}$ hydroxyalkyloxyalkyl group, a substituted or unsubstituted $C_3$–$C_{30}$ dialkylaminoalkyl group, a substituted or unsubstituted $C_6$–$C_{20}$ pyridylalkyl group, a substituted or unsubstituted $C_2$–$C_{10}$ lactone, a substituted or unsubstituted $C_2$–$C_{10}$ lactam, a substituted or unsubstituted pyridine, a substituted or unsubstituted imidazol, hydrazine, hydrozone, a substituted or unsubstituted $C_1$–$C_{20}$ pyridylalkyl group, a primary, secondary, or tertiary amine, a substituted or unsubstituted $C_6$–$C_{20}$ heteroaryl group, a substituted or unsubstituted $C_6$–$C_{20}$ heteroarylalkyl group, a substituted or unsubstituted $C_6$–$C_{20}$ heteroarylalkenyl group, and a substituted or unsubstituted $C_3$–$C_{20}$ heterocycloalkyl group.

In another aspect, the present invention provides an ink composition including the above 2-methoxyphenol derivative, an aqueous medium, and a colorant. The ink composition may contain 0.1–40 parts by weight of the 2-methoxyphenol derivative with respect to 100 parts by weight of the ink composition.

The aqueous medium of the ink composition may be water or a mixture of water and an organic solvent. The amount of the organic solvent in the aqueous medium may be in the range of 2–50 parts by weight with respect to 100 parts by weight of the ink composition.

Examples of the organic solvent for the ink composition include, but are not limited to, alcohols, such as methyl alcohol, ethyl alcohol, n-propyl alcohol, isopropyl alcohol, n-butyl alcohol, sec-butyl alcohol, t-butyl alcohol, isobutyl alcohol, etc.; ketones, such as acetone, methylethyl ketone, diacetone alcohol, etc.; esters, such as ethyl acetate, ethyl lactate, etc.; polyhydric alcohols, such as ethylene glycol, diethylene glycol, triethylene glycol, propylene glycol, butylene glycol, 1,4-butane diol, 1,2,4-butane triol, 1,5-pentane diol, 1,2-hexane diol, 1,6-hexane diol, 1,2,6-hexane triol, hexylene glycol, glycerol, glycerol ethoxylate, trimethylolpropane ethoxylate, etc.; lower alkyl ethers, such as ethylene glycol monomethyl ether, ethylene glycol monoethyl ether, diethylene glycol methyl ether, diethylene glycol ethyl ether, diethylene glycol methyl ether, diethylene glycol ethyl ether, triethylene glycol monomethyl ether, triethylene glycol monoethyl ether, etc.; nitrogen-containing compounds, such as 2-pyrrolidone, N-methyl-2-pyrrolidone, caprolactam, etc.; dimethyl sulfoxide; tetramethylene sulfone; and thioglycol.

The ink composition according to the present invention may further include at least one of a viscosity adjuster, a surfactant, a storage stabilizer, a metal oxide and a dispersant.

Additional aspects and/or advantages of the invention will be set forth in part in the description which follows and, in part, will be obvious from the description, or may be learned by practice of the invention.

DETAILED DESCRIPTION OF THE PREFERRED EMBODIMENTS

Reference will now be made in detail to the embodiments of the present invention.

A 2-methoxyphenol derivative according to the present invention is described in detail below. A 2-methoxyphenol derivative having formula (1) below according to the present invention absorbs or blocks ultraviolet (UV) light, provides wettability and stabilizes a colorant.

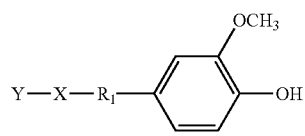

(1)

wherein $R_1$ is selected from among a substituted or unsubstituted $C_1$–$C_{20}$ alkylene group, a substituted or unsubstituted $C_1$–$C_{20}$ alkenylene group, a substituted or unsubstituted $C_1$–$C_{20}$ alkynylene group, a substituted or unsubstituted $C_6$–$C_{30}$ arylene group, a substituted or unsubstituted $C_6$–$C_{30}$ arylalkylene group, a substituted or unsubstituted $C_1$–$C_{30}$ heteroalkylene group, a substitute or unsubstituted $C_6$–$C_{30}$ heteroarylene group, and a substituted or unsubstituted $C_6$–$C_{30}$ heteroarylalkylene group;

X is selected from among —O—, —NR—, —N=N—, —S—, —P—, —C(=O)—NR—, —NR—C(=O)—, —S(=O)(=O)O—, —C(=O)O—, —O—C(=O)—, —P(=O)O—, —C(=O)—O—C(=O)—, —C(=O)—S—C(=O)—, —C(=)—NR—C(=O)—, —C(=NH)—O—C(=NH)—, —C(=S)—O—C(=S)—, —C(=NH)—NR—C(=NH)—, —C(=S)—NR—C(=S)—, —C(=NH)—S—C(=NH)—, and —C(=S)—S—C(=S)—;

R is a hydrogen atom or a $C_1$–$C_5$ alkyl group; and

Y is selected from among a substituted or unsubstituted $C_1$–$C_{20}$ alcohol, a substituted or unsubstituted $C_1$–$C_{20}$ diol, a substituted or unsubstituted $C_1$–$C_{20}$ triol, a substituted or unsubstituted $C_1$–$C_{20}$ polyhydric alcohol, a substituted or unsubstituted $C_2$–$C_{20}$ hydroxyalkyloxyalkyl group, a substituted or unsubstituted $C_3$–$C_{30}$ dialkylamonoalkyl group, a substituted or unsubstituted $C_6$–$C_{20}$ pyridylalkyl group, a substituted or unsubstituted $C_2$–$C_{10}$ lactone, a substituted or unsubstituted $C_2$–$C_{10}$ lactam, a substituted or unsubstituted pyridine, a substituted or unsubstituted imidazol, hydrazine, hydrozone, a substituted or unsubstituted $C_1$–$C_{20}$ pyridylalkyl group, a primary, secondary, or tertiary amine, a substituted or unsubstituted $C_6$–$C_{20}$ heteroaryl group, a substituted or unsubstituted $C_6$–$C_{20}$ heteroarylalkyl group, a substituted or unsubstituted $C_6$–$C_{20}$ heteroarylalkenyl group, and a substituted or unsubstituted $C_3$–$C_{20}$ heterocycloalkyl group.

Examples of an unsubstituted alkylene group for $R_1$ in formula (1) include, but are not limited to, a methylene group, an ethylene group, a propylene group, an isopropylene group, a butylene group, an isobutylene group, an isopentylene group, a neopentylene group, a hexylene group, an isohexylene group, an isoamyl group, cyclobutylene group, a cyclopentylene group, a cyclohexylene group, a cycloheptylene group, and the like.

An unsubstituted $C_1$–$C_{20}$ alkenylene or alkynylene group for $R_1$ in formula (1) includes a carbon double or triple bond in the middle or at the end of the alkylene group defined above. Examples of such an unsubstituted $C_1$–$C_{20}$ alkenylene or alkynylene group include ethylene, propylene, butylene, hexylene, acetylene, and the like. At least one hydrogen atom in the alkenylene or alkynylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_{20}$ alkenyl group, a $C_1$–$C_{20}$ alkynyl group, a $C_1$–$C_{20}$ heteroalkyl group, a $C_6$–$C_{20}$ aryl group, a $C_6$–$C_{20}$ arylalkyl group, a $C_6$–$C_{20}$ heteroaryl group, or a $C_6$–$C_{20}$ heteroarylalkyl group.

A heteroalkylene group for $R_1$ in formula (1) includes a nitrogen atom, sulfur atom, oxygen atom, or phosphorous atom in the alkylene group defined above. Examples of such a heteroalkylene group include a methoxy group, an ethoxy group, a propoxy group, a butoxy group, a t-butoxy group, and the like. Examples of a heteroalkylene group with a substituent include haloalkoxy radicals, such as fluoromethoxy, chloromethoxy, trifluoromethoxy, trifluoroethoxy, fluoroethoxy, fluoropropoxy, and the like. At least one hydrogen atom in the heteroalkylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_{20}$ alkenyl group, a $C_1$–$C_{20}$ alkynyl group, a $C_1$–$C_{20}$ heteroalky group, a $C_6$–$C_{20}$ aryl group, a $C_6$–$C_{20}$ arylalkyl group, a $C_6$–$C_{20}$ heteroaryl group, or a $C_6$–$C_{20}$ heteroarylalkyl group.

An arylene group for $R_1$ in formula (1), which may be used alone or in combination, refers to a $C_6$–$C_{30}$ carbocyclic system containing at least one ring wherein such rings may be attached together in a pendent manner or may be fused. The arylene group may have a substituent, such as hydroxy, halo, haloalkyl, nitro, cyano, alkoxy, lower alkylamino, and the like. At least one hydrogen atom in the arylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_{20}$ alkenyl group, a $C_1$–$C_{20}$ alkynyl group, a $C_1$–$C_{20}$ heteroalkyl group, a $C_6$–$C_{20}$ aryl group, a $C_6$–$C_{20}$ arylalkyl group, a $C_6$–$C_{20}$ heteroaryl group, or a $C_6$–$C_{20}$ heteroarylalkyl group. The term "aryl" implies aromatic radicals, such as phenyl, naphthyl, tetrahydronaphthyl, indane, biphenyl, and the like, wherein phenyl or haphthyl is preferred for the aryl group.

An arylalkylene group for $R_1$ in formula (1) refers to the above-defined arylene group having lower alkyl substitute radicals, for example, methyl, ethyl, propyl, and the like for some hydrogen atoms. Examples of such an arylalkylene group include benzyl, phenylethyl, etc. At least one hydrogen atom in the arylalkylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_2$0 alkenyl group, a $C_1$–$C_{20}$ alkynyl group, a $C_1$–$C_{20}$ heteroalkyl group, a $C_6$–$C_{20}$ aryl group, a $C_6$–$C_{20}$ arylalkyl group, a $C_6$–$C_{20}$ heteroaryl group, or a $C_6$–$C_{20}$ heteroarylalkyl group.

A heteroarylene group for $R_1$ in formula (1) refers to a $C_6$–$C_{30}$ carbocyclic system containing one, two, or three hetero atoms selected from the group consisting of N, O, P, and S, wherein the carbocyclic system may be monocyclic or bicyclic. Hetero atoms in the cyclic system may be oxidized or quaternarized to form, for example, N-oxide or a quaternary salt. Typical examples of such a heteroarylene group include, but are not limited to, tienyl, benzotienyl, pyridyl, pyrazinyl, pyrimidinyl, pyridazinyl, quinolinyl, quinoxalinyl, furanyl, benzofuranyl, thiazolyl, isoxazolyl, benzisoxazolyl, benzimidazolyl, triazolyl, pyrazolyl, purrolyl, indolyl, 2-pyridonyl, 4-pyridonyl, N-alkyl-2-pyrinonyl, pyrazinonyl, pyridazinonyl, pyrimidinonyl, oxazolonyl, an N-oxide of the foregoing groups, such as pyridyl N-oxide and quinolinyl N-oxide, and a quaternary salt of the foregoing groups. At least one hydrogen atom in the heteroarylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_{20}$alkenyl group, a $C_1$–$C_{20}$ alkynyl group, a $C_1$–$C_{20}$ heteroalkyl group, a $C_6$–$C_{20}$ aryl group, a $C_6$–$C_{20}$ arylalkyl group, a $C_6$–$C_{20}$ heteroaryl group, or a $C_6$–$C_{20}$ heteroarylalkyl group.

A heteroarylalkylene group for $R_1$ in formula (1) refers to the above-defined heteroarylene group having alkylene groups. At least one hydrogen atom in the heteroarylalkylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_{20}$ alkenyl group, a $C_1$–$C_{20}$ alkynyl group, a $C_1$–$C_{20}$ heteroalkyl group, a $C_6$–$C_{20}$ aryl group, a $C_6$–$C_{20}$ arylalkyl group, a $C_6$–$C_{20}$ heteroaryl group, or a $C_6$–$C_{20}$ heteroarylalkyl group.

In formula (1) above, Y provides wettability and the ability to stabilize a colorant. As described above, Y in formula (1) is selected from among a substituted or unsubstituted $C_1$–$C_{20}$ alcohol, a substituted or unsubstituted $C_1$–$C_{20}$ diol, a substituted or unsubstituted $C_1$–$C_{20}$ triol, a substituted or unsubstituted $C_1$–$C_{20}$ polyhydric alcohol, a substituted or unsubstituted $C_2$–$C_{20}$ hydroxyalkyloxyalkyl group, a substituted or unsubstituted $C_3$–$C_{30}$ dialkylamonoalkyl group, a substituted or unsubstituted $C_6$–$C_{20}$ pyridylalkyl group, a substituted or unsubstituted $C_2$–$C_{10}$ lactone, a substituted or unsubstituted $C_2$–$C_{10}$ lactam, a substituted or unsubstituted pyridine, a substituted or unsubstituted imidazol, hydrazine, hydrozone, a substituted or unsubstituted $C_1$–$C_{20}$ pyridylalkyl group, a primary, secondary, or tertiary amine, a substituted or unsubstituted $C_6$–$C_{20}$ heteroaryl group, a substituted or unsubstituted $C_6$–$C_{20}$ heteroarylalkyl group, a substituted or unsubstituted $C_6$–$C_{20}$ heteroarylalkenyl group, and a substituted or unsubstituted $C_3$–$C_{20}$ heterocycloalkyl group.

Hereinafter, an ink composition containing the 2-methoxyphenol derivative of formula (1) will now be described in detail.

An ink composition according to an embodiment of the present invention includes an aqueous medium, a colorant, such as a dye or a pigment, and an additive that provides wettability and stabilizes a colorant. The 2-methoxyphenol derivative of formula (1) may be used for the additive. The amount of the compound of formula (1), which provides wettability and stabilizes a colorant, may be in the range of 0.1–40 parts by weight with respect to 100 parts by weight of the ink composition.

Water may be used alone for the aqueous medium of the ink composition according to an embodiment of the present invention. Alternatively, a mixture of water and an organic solvent may be used for the aqueous medium. In this case, the amount of the organic solvent may be in the range of 2–50 parts by weight with respect to 100 parts by weight of the ink composition. The amount of the organic solvent in the aqueous medium may be adjusted to provide an appropriate viscosity and surface tension to the ink composition.

The organic solvent may be at least one hydrocarbon solvent selected from the group consisting of alcohols, such as methyl alcohol, ethyl alcohol, n-propyl alcohol, isopropyl alcohol, n-butyl alcohol, sec-butyl alcohol, t-butyl alcohol, isobutyl alcohol, etc.; ketones, such as acetone, methylethyl ketone, diacetone alcohol, etc.; esters, such as ethyl acetate, ethyl lactate, etc.; polyhydric alcohols, such as ethylene glycol, diethylene glycol, triethylene glycol, propylene glycol, butylene glycol, 1,4-butane diol, 1,2,4-butane triol, 1,5-pentane diol, 1,2-hexane diol, 1,6-hexane diol, 1,2,6-hexane triol, hexylene glycol, glycerol, glycerol ethoxylate, trimethylolpropane ethoxylate, etc.; lower alkyl ethers, such as ethylene glycol monomethyl ether, ethylene glycol monoethyl ether, diethylene glycol methyl ether, diethylene glycol ethyl ether, diethylene glycol methyl ether, diethylene glycol ethyl ether, triethylene glycol monomethyl ether, triethylene glycol monoethyl ether, etc.; nitrogen-containing compounds, such as 2-pyrrolidone, N-methyl-2-pyrrolidone, caprolactam, etc.; dimethyl sulfoxide; tetramethylene sulfone; and thioglycol.

The ink composition according to an embodiment of the present invention may further include an additive, for example, a dispersant, a viscosity adjuster, a surfactant, a storage stabilizer or a metal oxide.

The surfactant of the ink composition affects the surface tension of the composition to provide more stable jettability when the composition is sprayed via a nozzle. An anionic surfactant, cationic surfactant or a nonionic surfactant may be used for the surfactant. The amount of the surfactant may be in the range of 0.1–5.0 parts by weight with respect to 100 parts by weight of the ink composition.

The viscosity adjuster of the ink composition ensures a smoother jetting process through viscosity adjustment. One of polyvinyl alcohol, casein, carboxymethylcellulose may be used for the viscosity adjuster. The amount of the viscosity adjuster may be in the range of 0.5–5.0 parts by weight with respect to 100 parts by weights of the ink composition.

Any dye and pigment that are commonly used for ink compositions may be used for the colorant of the ink composition according to an embodiment of the present invention. Specific examples of a dye for the colorant include, but are not limited to, C.I Direct Black Nos. 9, 17, 19, 22, 32, 56, 91, 94, 97, 166, 168, 174, and 199; C.I Direct Blue Nos. 1, 10, 15, 22, 77, 78, 80, 200, 201, 202, 203, 207, and 211; C.I Direct Red Nos. 2, 4, 9, 23, 31, 39, 63, 72, 83, 84, 89, 111, 173, 184, and 240; and C.I Direct Yellow Nos. 8, 9, 11, 12, 27, 28, 29, 33, 35, 39, 41, 44, 50, 53, and 58. Specific examples of a pigment for the colorant include, but are not limited to, carbon black, graphite, vitreous carbon, activated charcoal, activated carbon, anthraquinone, phthalocyanine blue, phthalocyanine green, diazos, monoazos, pyranthrones, perylene, quinacridone, and indigoid pigments.

In particular, both inorganic and organic pigments may be used. The particle diameter of colorants significantly affects wettability, color strength, and glossiness. Accordingly, the pigment for the colorant may have a particle diameter of 0.1–1.0 μm that is small enough to pass a nozzle.

The amount of the colorant may be in the range of 0.1–20 parts by weight, preferably, 0.5–15 parts by weight, with respect to 100 parts by weight of the ink composition.

The ink composition of an embodiment of the present invention may further include an acid or a base to increase the solubility of the additive, acting as a wetting agent, in the solvent and stabilize the pigment in the ink composition. The amount of the acid or base may be in the range of 0.1–20 parts by weight with respect to 100 parts by weight of the ink composition.

The above ink composition according to an embodiment of the present invention may be prepared as follow. Initially, a colorant, the 2-methoxyphenol derivative of formula (1) above, and additionally additives such as viscosity adjuster and surfactant are added to an aqueous medium and thoroughly mixed using a stirrer to homogenize. The resultant mixture is passed through a filter to provide an ink composition according to an embodiment of the present invention.

The 2-methoxyphenol derivative of formula (1) according to embodiments of the present invention may be used for, but is not limited to, toner compositions, various paints, coating solutions, etc., in addition to ink compositions.

Embodiments of the present invention are described below in greater detail with reference to the following examples. The following examples are for illustrative purposes and are not intended to limit the scope of the invention. Although the following examples are described with reference to ink compositions containing the 2-methoxyphenol derivative of formula (1), it will be appreciated that the present invention is not limited to these ink compositions and that experimental methods used to evaluate the properties of the ink compositions may be applied to wet toners, dry toners, paints, and coating solutions.

SYNTHETIC EXAMPLE 1

(1) 100 mL of chloroform was placed into a 250-mL round-bottomed flask and bubbled while supplying a HCl gas for 1–2 hours, and 29.5 g of 2-methoxy-4-(2-propenyl) phenol was added to the flask and refluxed for 6 hours or longer. 16.6 g of NaCN was added to the reaction solution and reacted at 80° C. for 8 hours or longer to extract the organic phase. The organic phase was concentrated to obtain 37.5 g of a crystalline compound A.

(2) 30.6 g of the crystalline compound (A) was dissolved in 500 mL of a 1:1 mixture of water and methanol. 30 mL of concentrated sulfuric acid were slowly added together with one or two boiling chips into the mixture and refluxed for 10 hours or longer. The reaction solution was cooled to room temperature, and excess distilled water was added to precipitate a crystalline compound (B). The crystalline compound (B) was collected using a suction filter and was dried in an oven to provide 23.5 g of a compound of formula (2) below.

(3) 18.8 g of the compound of formula (2) was dissolved in 100 mL of ethyl acetate contained in a 250-mL round-bottomed flask, and 9.6 g of glycerin was added into the solution. 20 mL of concentrated sulfuric acid was slowly dropped together with one or two boiling chips into the solution and refluxed for 12 hours or longer. The resultant reaction solution was cooled to room temperature, and excess methanol was added to precipitate a crystalline compound, followed by suction filtration. The crystalline compound was dissolved in dimethylsulfoxide (DMSO) to remove the unreacted reactant, and methanol was added to the solution to precipitate a crystalline compound. This crystalline compound was collected using a suction filter and was dried in an oven to provide 15.3 g of a compound of formula (3) below.

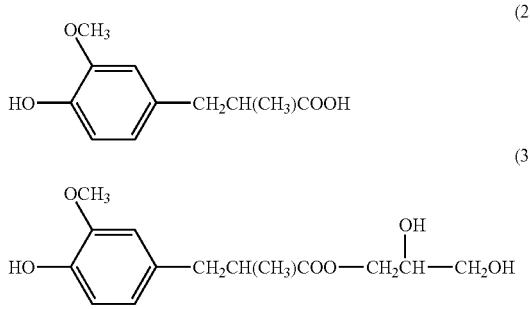

(2)

(3)

SYNTHESIS EXAMPLE 2

(1) 73.4 g of 2-methoxy-4-(2-propenyl)phenol was fully dissolved in 200 mL of dimethyl acetamide (DMAC) contained in a 500-mL Erlenmeyer flask. 74.2 g of perbenzoic acid was added to the solution and reacted at 80° C. for 12 hours or longer. The reaction solution was cooled to room temperature, and excess distilled water was added to precipitate a crystalline compound (C). The crystalline compound (C) was collected using a suction filter and dried in an oven to provide 57.2 g of epoxide.

(2) 9.9 g of ethylene glycol was added to, and thoroughly mixed with, 100 mL of DMSO contained in a 250-mL Erlenmeyer flask. 21.9 g of the epoxide was added to and dissolved in the mixture, reacted 80° C. for 8 hours or longer, and cooled to room temperature. Excess distilled water was added to the solution to precipitate a crystalline compound. This crystalline compound was collected using a suction filter and dried in an oven to provide 17.6 g of a compound of formula (4) below.

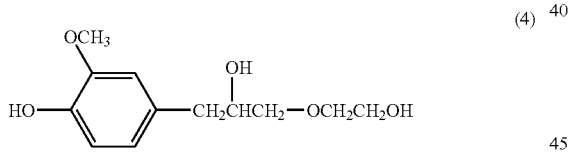

(4)

SYNTHESIS EXAMPLE 3

15.22 g of 4-ethyl-2-methoxyphenol was reacted with $Cl_2$ in the presence of a photocatalyst and then reacted with 6.21 g of ethylene glycol in the presence of a base to provide 14.86 g of a compound of formula (5) below.

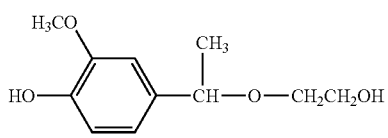

(5)

SYNTHESIS EXAMPLE 4

13.8 g of a compound of formula (6) below was synthesized in the same manner as in (3) of Synthesis Example 1, except that 18.5 g of the compound of formula (2) and 6.5 g of ethylene glycol were used.

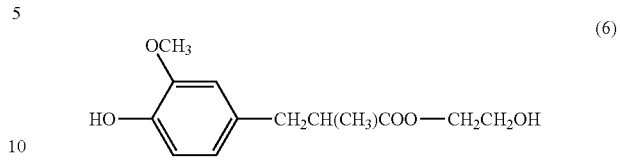

(6)

SYNTHESIS EXAMPLE 5

14.7 g of a compound of formula (7) below was synthesized in the same manner as in (3) of Synthesis Example 1, except that 17.2 g of the compound of formula (2) and 9.2 g of diethylene glycol were used.

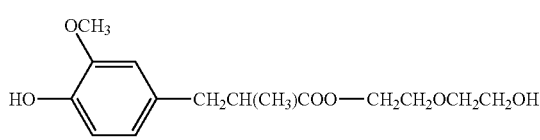

(7)

SYNTHESIS EXAMPLE 6

18.1 g of a compound of formula (8) below was synthesized in the same manner as in (2) of Synthesis Example 2, except that 19.7 g of the epoxide obtained in (1) of Synthesis Example 2 and 13.2 g of glycerin were used.

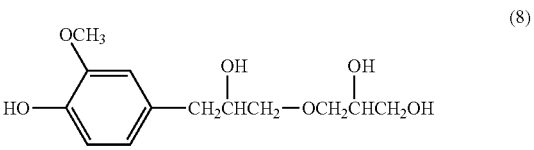

(8)

SYNTHESIS EXAMPLE 7

(1) 100 mL of chloroform was placed into a 250-mL round-bottomed flask and bubbled while supplying a HCl gas for 1–2 hours, and 29.5 g of 2-methoxy-4-(2-propenyl) phenol was added to the flask, refluxed for 6 hours or longer, and concentrated to provide 27.5 g of a crystalline compound of formula (D) below.

(2) 13.8 g of diethylene glycol was thoroughly mixed with 100 mL of DMSO, and 20.7 g of the crystalline compound (D) was dissolved in the mixture, reacted at 80° C. for 8 hours or longer, and concentrated to obtain a solution (E). This concentrated solution was dissolved in ether and washed with distilled water several times to extract the ether phase. This ether phase was reconcentrated to provide 17.2 g of a compound of formula (9) below.

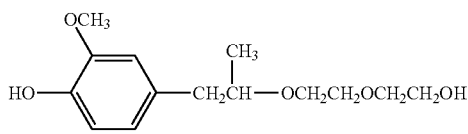

(9)

SYNTHESIS EXAMPLE 8

28.0 g of a 2-methoxyphenol derivative having formula (10) below was dissolved in 100 mL of DMSO contained in a 250-mL Erlenmeyer flask. 14.2 g of a polyhydric alcohol having formula (11) below was added into the solution, reacted at 120° C. for 8 hours or longer, and concentrated. This concentrated solution was dissolved in ether and washed with distilled water several times to extract the ether phase. This ether phase was reconcentrated to provide 19.5 g of a compound of formula (12) below.

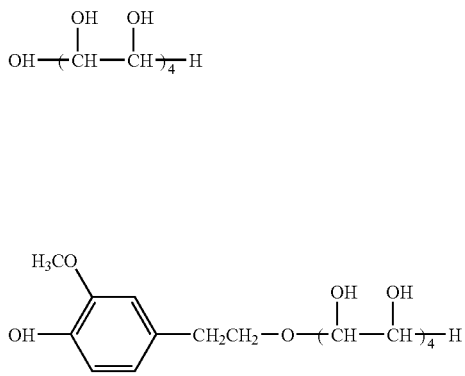

(10)

(11)

(12)

SYNTHESIS EXAMPLE 9

17.6 g of 3-(diethylamino)propionic acid was dissolved in 50 mL of DMSO contained in a 250-mL Erlenmeyer flask. 14.3 g of $SOCl_2$ was added to the solution and reacted at room temperature for 1 hour or longer to provide a solution (A). A solution of 16.9 g of a 2-methoxyphenol derivative having formula (13) below in 50 mL of DMSO was added to the solution (A) together with one or more boiling chips and refluxed at 80° C. for 6 hours or longer. The resulting reaction solution was cooled to room temperature, and excess methanol was added to the reaction solution to precipitate a crystalline compound, followed by suction filtration. This crystalline compound was dissolved in DMSO to remove the unreacted reactant, and methanol was added to the solution to separate a crystalline compound, followed by suction filtration and drying to provide 17.1 g of a compound of formula (14) below.

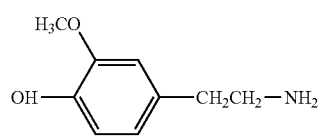

(13)

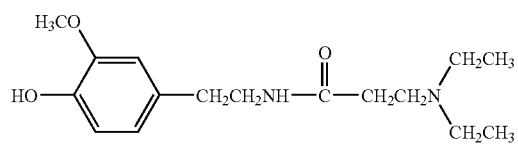

(14)

SYNTHESIS EXAMPLE 10

18.3 g of a compound having formula (16) below was synthesized in the same manner as in Synthesis Example 9, except that 21.9 g of a 2-methoxyphenol derivative having formula (15) below and 12.7 g of 3,4-dihydroxy butylic acid were used.

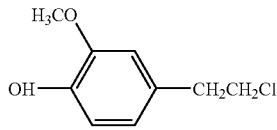

(15)

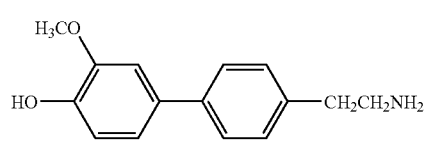

(16)

SYNTHESIS EXAMPLE 11

17.2 g of a 2-methoxyphenol derivative having formula (17) below and 18.6 g of 3-(3-tienyl) acrylic acid were dissolved in 100 mL of ethyl acetate contained in a 250-mL round-bottomed flask. 10 mL of concentrated sulfuric aid was slowly dropped together with one or two boiling chips into the solution and refluxed for 12 hours or longer. The organic phase was separated from the solution using distilled water, concentrated, and recrystallized to provide 17.3 g of a compound having formula (18) below.

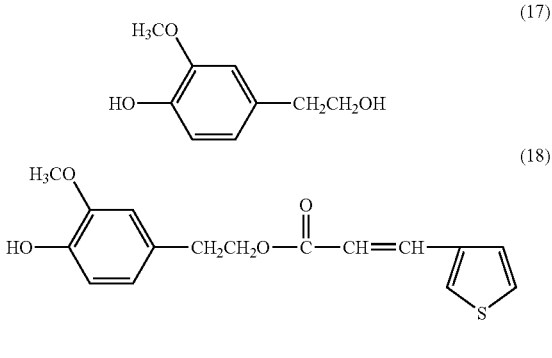

(17)

(18)

SYNTHESIS EXAMPLE 12

17.6 g of a compound having formula (20) below was synthesized in the same manner as in Synthesis Example 8, except that 21.3 g of a 2-methoxyphenol derivative having formula (19) below and 15.5 g of thiazolyl-4-carboxylic acid were used.

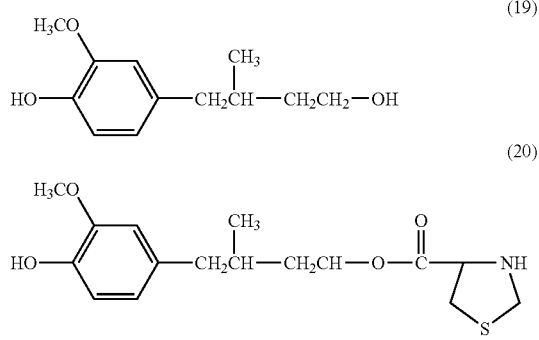

(19)

(20)

SYNTHESIS EXAMPLE 13

19.1 g of a compound having formula (22) below was synthesized in the same manner as in Synthesis Example 8, except that 22.1 g of a 2-methoxyphenol derivative having formula (21) below and 15.7 g of 2-pyridine propanol were used.

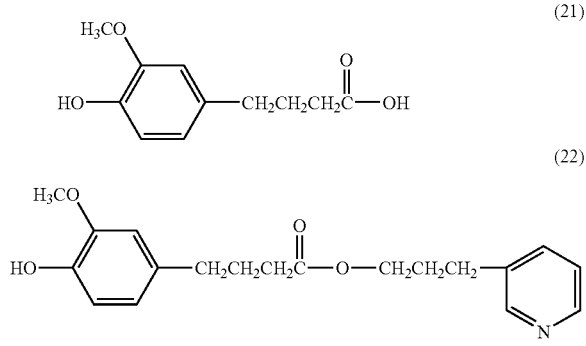

(21)

(22)

SYNTHESIS EXAMPLE 14

16.6 g of a compound having formula (23) below was synthesized in the same manner as in Synthesis Example 8, except that 15.1 g of the 2-methoxyphenol derivative of formula (17) above and 16.0 g of 2-pyrrolidone-5-caboxylic acid were used.

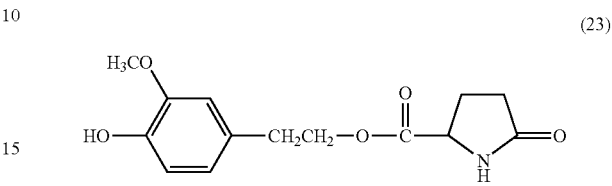

(23)

EXAMPLE 1

An ink composition having the following composition was prepared.

| Component | Content |
| --- | --- |
| Colorant (C.I Direct Black 9) | 4.0 g |
| Water | 77.0 g |
| Isopropyl alcohol | 3.0 g |
| Ethylene glycol | 8.0 g |
| Compound of formula (3) | 8.0 g |

EXAMPLES 2–14

Ink compositions were prepared according to the same composition as in Example 1, except that the compounds of formulae (4), (5), (6), (7), (8), (9), (12), (14), (16), (18), (20), (22), and (23) were respectively used instead of the compound of formula (3).

COMPARATIVE EXAMPLES 1–8

Ink compositions were prepared according to the same composition as in Example 1, except that glycerin, ethylene glycol, the polyhydric alcohol of formula (11), 3,4-dihydroxy butylic acid, 3-(3-tienyl)acrylic acid, thiazolyl-4-carboxylic acid, 2-pyridine propanol, 2-pyrrolidone-5-carboxylic acid were respectively used instead of the compound of formula (3), 0.5 g of {Irganox} IRGANOX 245DW (available from CIBA CO.) was further added, and the amount of water was reduced by 0.5 g.

The properties of the ink compositions prepared in Examples 1 through 14 and Comparative Examples 1 through 8 were evaluated as follows.

Long-term Storage Stability Test 100 mL of samples of the ink compositions prepared in Examples 1 through 14 and Comparative Examples 1 through 8 were portioned into respective heat-resistant glass bottles. The glass bottles were sealed and stored in a 60° C.-convection oven for 2 months. It was observed whether precipitates appeared in the bottles. The results are shown in Tables 1 and 2. In Tables 1 and 2, "0" indicates no precipitates appear, and "X" indicates that precipitates appear.

TABLE 1

| Example No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Result | 0 | 0 | 0 | 0 | 0 | 0 | 0 | 0 | 0 | 0 | 0 | 0 | 0 | 0 |

TABLE 2

| Comparative Example No. | 1 | 2 | 3 | 4 | 5 | 6 | 7 | 8 |
|---|---|---|---|---|---|---|---|---|
| Result | X | X | X | X | X | X | X | X |

Light Resistance Test

Ink cartridges (available from SAMSUNG ELECTRONICS CO., LTD.) were filled with the respective ink compositions of Examples 1 through 14 and Comparative Examples 1 through 8. After printing 2×2 cm solid patterns using the ink cartridges, the printed results were exposed to light for 100 hours in a Q-SUN XENON TEST CHAMBER. Optical density (OD) was measured before and after light exposure, and A values were calculated using the following equation. Light resistance was evaluated as 0 for $A \geq 90$, $\Delta$ for $75 \leq A < 90$, and X for $A < 75$. The results are shown in Tables 3 and 4.

$A = OD$ after test/$OD$ before test×100(%)

TABLE 3

| Example No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Result | 0 | 0 | 0 | 0 | 0 | 0 | 0 | 0 | 0 | 0 | 0 | 0 | 0 | 0 |

TABLE 4

| Comparative Example No. | 1 | 2 | 3 | 4 | 5 | 6 | 7 | 8 |
|---|---|---|---|---|---|---|---|---|
| Result | Δ | Δ | 0 | 0 | 0 | Δ | 0 | 0 |

As described above, a 2-methoxyphenol derivative having formula (1) above according to an embodiment of the present invention absorbs UV light, provides wettability and stabilizes a colorant. In addition, when the 2-methoxyphenol derivative is used to prepare an ink composition, the ink composition has improved light resistance and wettability and stabilizes a colorant.

Although a few embodiments of the present invention have been shown and described, it would be appreciated by those skilled in the art that changes may be made in this embodiments without departing from the principles and spirit of the invention, the scope of which is defined in the claims and their equivalents.

What is claimed is:

1. A composition comprising:
   a functional additive being a 2-methoxyphenol derivative having formula (1) below:

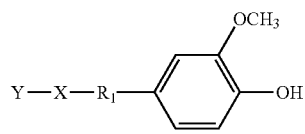

wherein $R_1$ is an unsubstituted $C_1$–$C_{20}$ alkylene;
X is —O—; Y is an unsubstituted $C_1$–$C_{20}$ alcohol;
a functional aqueous medium that is a solvent that is water; and
a functional colorant comprising a black-based dye to provide a black color.

2. The composition of claim 1, wherein the amount of the 2-methoxyphenol derivative is in a range of 0.1–40 parts by weight with respect to 100 parts by weight of the composition.

3. The composition of claim 1, further comprising at least one selected from the group consisting of a viscosity adjuster, a surfactant, a storage stabilizer, a metal oxide and a dispersant.

4. The composition of claim 1, wherein the 2-methoxyphenol derivative has the formula (5) below:

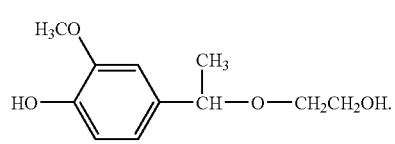

5. The composition of claim 1, wherein the 2-methoxyphenol derivative has the formula (12) below:

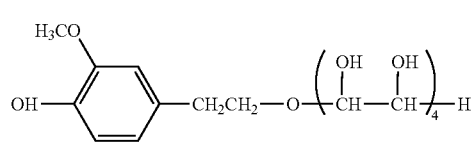

* * * * *